(12) United States Patent
Speckner et al.

(10) Patent No.: US 11,662,411 B2
(45) Date of Patent: May 30, 2023

(54) MAGNETIC RESONANCE (MR)-SCANNER CONTROL

(71) Applicant: Siemens Healthcare GmbH, Erlangen (DE)

(72) Inventors: Thorsten Speckner, Erlangen (DE); Swen Campagna, Engelthal (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/519,200

(22) Filed: Nov. 4, 2021

(65) Prior Publication Data
US 2022/0137172 A1 May 5, 2022

(30) Foreign Application Priority Data
Nov. 5, 2020 (DE) .......................... 102020213920.2

(51) Int. Cl.
*G01V 3/00* (2006.01)
*G01R 33/54* (2006.01)
(Continued)

(52) U.S. Cl.
CPC ............ *G01R 33/543* (2013.01); *A61B 5/055* (2013.01); *G01R 33/5608* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 7,937,163 B2   5/2011 Sekiguchi
2005/0043614 A1* 2/2005 Huizenga ............. A61B 5/7235
                                                    600/427
(Continued)

FOREIGN PATENT DOCUMENTS

| CN | 1701336 A | * | 11/2005 | ............... E02D 1/02 |
| DE | 102016225793 B3 | * | 2/2018 | ............. A61B 5/055 |
| WO | WO-2016030393 A1 | * | 3/2016 | ........... G09B 23/288 |

OTHER PUBLICATIONS

German Action dated Jul. 16, 2021, Application No. 10 2020 213 920.2.

*Primary Examiner* — Walter L Lindsay, Jr.
*Assistant Examiner* — Frederick Wenderoth
(74) *Attorney, Agent, or Firm* — Banner & Witcoff Ltd.

(57) ABSTRACT

Techniques are described for controlling a fleet of MR-scanner systems by means of a user interface. Each MR scanner system in the fleet of MR scanner systems comprises a hardware layer having a plurality of electronically controllable components and mechanical components to perform an MR measurement and capture MR-scanner raw data, a Measurement And Reconstruction System (MARS) computing unit configured to implement a measurement framework using a sequence to calculate real-time instructions and transmit these instructions to the components of the hardware layer for controlling the MR-scanner system, and a communication interface for communicating with an external device. Each MR scanner system has system attributes, which are transmitted to the external device via the communication interface.

15 Claims, 2 Drawing Sheets

(51) Int. Cl.
  *G01R 33/56* (2006.01)
  *G01R 33/561* (2006.01)
  *A61B 5/055* (2006.01)
  *G16H 30/20* (2018.01)
  *G16H 40/63* (2018.01)
  *G16H 30/40* (2018.01)

(52) U.S. Cl.
  CPC ......... *G01R 33/5611* (2013.01); *G16H 30/20* (2018.01); *G16H 30/40* (2018.01); *G16H 40/63* (2018.01)

(58) Field of Classification Search
  USPC .......................................... 324/309
  See application file for complete search history.

(56) References Cited

U.S. PATENT DOCUMENTS

| | | |
|---|---|---|
| 2006/0036555 A1 | 2/2006 | Beck et al. |
| 2007/0273310 A1* | 11/2007 | Foch .................. H02P 6/04 318/112 |
| 2010/0063834 A1* | 3/2010 | Mukherjee ............. G16H 15/00 705/2 |
| 2018/0330818 A1 | 11/2018 | Hsieh et al. |
| 2018/0336964 A1 | 11/2018 | Westin et al. |

* cited by examiner

MAGNETIC RESONANCE (MR)-SCANNER CONTROL

CROSS-REFERENCE TO RELATED APPLICATIONS

The present application claims the benefit of the filing date of Germany patent application no. DE 10 2020 213 920.2, filed on Nov. 5, 2020, the contents of which are incorporated herein by reference in their entirety.

TECHNICAL FIELD

The disclosure relates to the technical field of MR-scanner control and, in particular, to a method for controlling a fleet of MR-scanner systems by means of a user interface. The present disclosure also relates to a system for controlling a fleet of MR-scanner systems, and to a method for reconstructing images from MR-scanner raw data captured by at least one MR-scanner system from a fleet of MR-scanner systems controlled by the aforementioned method. In addition, the present disclosure relates to a computer program product.

BACKGROUND

MR-scanner systems for performing magnetic resonance tomography (MRT) as a non-invasive imaging technique are increasingly important in the field of medical diagnostics. MR-scanner systems may be used to depict different contrasts resulting from different physical and physiological properties of tissue, and the images reconstructed from the raw data can be utilized for medical diagnostics.

SUMMARY

Conventional MR-scanner systems comprise a MR device containing the physical components such as coils, RF receivers, etc. and an MR electronics unit, which is controlled by means of real-time instructions. A conventional MR-scanner system also comprises two further components: a MARS processing unit (MARS: Measurement And Reconstruction System) and a host computer. The host computer is thus a local element of the MR system and imports the system attributes of the MR device, and has a user interface to create specifications for the MARS processing unit to calculate real-time instructions for transfer to the MR electronics unit for the purpose of controlling the MR device.

As part of consolidation in the healthcare system, the number of organizations running corresponding radiology centers and departments in hospitals is increasing. The radiology centers and departments have a constantly-increasing number of deployable MR-scanner systems. For the organizations running the MR-scanner systems, this results in a potential for synergy because the systems may generally be used for the same diagnostics. The systems, however, are heterogeneous in terms of both their physical construction and the mechanical components used, and therefore are very different in design, which in existing systems may cause problems with consistency with respect to control or management.

In addition, the growth in the number of MR-scanner systems being used (e.g. within a fleet) may make a high degree of standardization necessary. This is against the background that the general hardware or the physics of the MR-scanner systems remains practically constant or unchanged over several development generations, whereas the version of the software used on the different MR-scanner systems for both planning an MR measurement and performing a measurement may differ, and hence some or all of the range of functions of this software may also differ. As a result, a user (e.g. a radiologist, a technician, etc.) should have specific knowledge to operate one MR-scanner system, and should have different and/or additional knowledge for another MR-scanner system to be able to operate these MR-scanner systems and perform specific MR measurements and/or configuration actions.

As a result of different software versions for MR-scanner systems of possibly identical construction, it may be the case that the installed software for scanners of a younger generation is adapted specifically to these scanners and/or has been suitably adjusted/modified by an optimization process. Equally, newer software versions can deliver and provide new and more extensive functions.

In addition, it is complicated to develop suitable updates and, if necessary, upgrades to be able to run each MR-scanner system with the same software version, and the separate rollout of new software versions for each MR-scanner system is often complex and lasts a period of several months.

Furthermore, a technician on site and/or a stable remote connection is required for the rollout of new software versions to be able to install the new software version. This usually entails a facility being out of action, which can last several hours or days.

Against this background, the technical object of the present disclosure is to overcome at least some of the disadvantages known in the art, and to provide a solution that makes possible, and makes more flexible, operation (control and running) of MR-scanner systems that have the same physics but a different software status.

This object is achieved by the subject matter as described herein and in the claims, e.g. via a method and system for controlling a fleet. The claims and the following description define advantageous embodiments of the disclosure. Advantageous embodiments and developments appear in the claims and in the description with reference to the figures.

Techniques are described herein for controlling a fleet of MR-scanner systems by means of a user interface. Each MR scanner system in the fleet of MR scanner systems comprises a hardware layer having a plurality of electronically controllable components and mechanical components to perform an MR measurement and capture MR-scanner raw data, a Measurement And Reconstruction System (MARS) computing unit configured to implement a measurement framework using a sequence to calculate real-time instructions and transmit these instructions to the components of the hardware layer for controlling the MR-scanner system, and a communication interface for communicating with an external device. Each MR scanner system has system attributes, which are transmitted to the external device via the communication interface. On the external device is formed the user interface configured to edit parameters for creating a protocol for a sequence, which can be implemented on an MR-scanner system, according to the transmitted system attributes of the MR-scanner system. The created protocol and the implementable sequence are transferred via the communication interface to the MARS computing unit for calculating the real-time instructions for controlling one (or a plurality of) MR-scanner system(s) in the fleet of MR-scanner systems.

According to a first aspect, the present disclosure relates to a method for controlling a fleet of MR-scanner systems via a user interface. An MR-scanner system shall be understood to mean an MR-scanner having suitable hardware for capturing raw data. MR-scanner systems are generally known. Known MR-scanner systems are characterized in that both the hardware that captures the raw data and the hardware and software that process the raw data is housed at the location of, or relatively local to, the measurement system. An MR-scanner system may be connected to one MR-scanner system or to a plurality of MR-scanner systems to form a fleet of MR-scanner systems, and may be controlled and operated locally by one or more users.

Within the meaning of the present disclosure, a user interface (UI) refers to an interface by means of which a user and/or operator interact with the MR-scanner system; a UI may also be in the form of a graphical user interface (GUI), for instance. By entering certain system states via the user interface (also known as a human machine interface—HMI), the user and/or operator may monitor the control and/or operation of the MR-scanner system, and accordingly manipulate the capture of the MR-scanner raw data by the MR-scanner system. The user interface is designed e.g. to create a protocol for a specific sequence. For this purpose, it is necessary to know system attributes of the particular MR-scanner (e.g. maximum gradient amplitude, maximum pulse duty factors, B1 amplitude, etc.) to be able to create a valid and consistent protocol parameter dataset for the particular type of scanner. Thus, the UI is generated specifically to take into account the system attributes of the scanner concerned so that configurations specific to the MR-scanner can be input and output at the UI.

An important technical advantage is that the UI is generated on the external device in such a way that also a plurality of users can work in parallel, and each individual user has dedicated control of a specific scanner. The respective UIs will typically be different because the associated scanners also differ in terms of their system attributes. Hence, there is an n-x-m association: n users control m scanners via a central processing unit (in this case an external device). The external device provides a specific GUI for each different user.

According to the disclosure, each MR-scanner system in the fleet of MR-scanner systems comprises a hardware layer having a plurality of electronically-controllable components and mechanical components to perform an MR measurement and capture MR-scanner raw data. Within the meaning of the present disclosure, the hardware layer of an MR-scanner system comprises the hardware components necessary for performing the medical examination, for instance the patient system etc., and for capturing MR-scanner raw data, for instance the coils, etc. The electronically-controllable components comprise parts necessary for implementing and/or configuring the parameters configured for the gradient system (TX, RX) and/or the patient system such that a predetermined MR measurement can be executed. The mechanical components are the components that are driven mechanically and/or electro-mechanically for an MR measurement and/or form part of the structure of the MR-scanner system.

Within the meaning of the disclosure, MR-scanner raw data refers to the data acquired by the magnetic resonance coil elements during an MR measurement, and from which are reconstructed by reconstruction the images that can be used for a medical diagnosis.

The MR-scanner system also comprises a Measurement and Reconstruction System MARS computing unit (MARS). The MARS computing unit is configured to implement a measurement framework using a sequence to calculate real-time instructions. The calculated real-time instructions are transmitted to the components of the hardware layer for controlling the MR-scanner system.

The MARS computing unit may be in the form of a computer, for example a workstation (PC) as is generally known in. The MARS computing unit has different interfaces for configuration, communication, and control. The MARS computing unit also has a processor unit for executing program code (e.g. machine-readable instructions).

The measurement framework interconnects the electronic components and generates the real-time instructions for controlling the electronically controllable components. The program instructions are converted from the abstract information in the sequence and the protocol into hardware signals (e.g. analog signals and/or machine code). The real-time instructions are transferred via dedicated real-time hardware to the electronically-controllable components in real time during the MR measurement.

Within the meaning of the present disclosure, the system attributes refer to the information on the maximum performance capability of the components of the MR-scanner system for the particular radiological examination to be executed. The system attributes are known a priori to be able to create a protocol for a sequence. The respective construction-related and/or performance-related limits for each of the components are defined by means of the sequence. The configurable parameters that may be used for a specific MR-scanner system are ultimately obtained via the sequence. Hence, this specifies the parameters that may be applied and implemented on an MR-scanner system at run-time.

The real-time instructions comprise instructions that are generated by the measurement framework. The measurement framework transmits the real-time instructions to the components of the hardware layer at a specific time instant. The real-time instructions may comprise, for instance, RF pulses (e.g. magnetic resonance excitation signals), which are generated by the measurement framework over a defined time interval at a specific time instant during the MR measurement. The real-time instructions may also specify at what time instant and at what interval relevant gradients are meant to be activated, and when a readout is meant to take place.

In addition, an MR-scanner system comprises a communication interface. The MR-scanner system may be connected to and communicate with an external device via the communication interface. The external device may be a workstation having an output unit and peripheral devices, a terminal having peripheral devices, or a touchscreen having input and output functionality.

The system attributes are transmitted to the external device via the communication interface. The system attributes comprise the attributes of the MR-scanner system, which constitute the limiting component for an MR measurement and are accordingly incorporated in the calculation of the real-time instructions. The external device reads out and/or provides and receives the system attributes of the MR-scanner system via a suitable interface. The system attributes comprise the attributes of the hardware layer, for instance the gradient strength or the power capability of the RF amplifier.

It is also provided that the user interface is generated on the external device, and e.g. is generated specifically for the particular application. Alternatively, the user interface may be implemented as the external device. The UI is generated such that the UI is designed to edit parameters for creating a protocol for a sequence, which may be implemented on an MR-scanner system according to the transmitted system attributes of the MR-scanner system.

Within the meaning of the present disclosure, parameters refer to the values that a user may wish to use for a radiological examination (assessment) and that are transferred to the MR-scanner system via a suitable interface. The protocol is obtained from the transferred parameters. The protocol thus comprises the parameters that a user has set for a radiological examination. The parameters specified in the protocol are defined by the approaching sequence according to the particular MR-scanner system and, if necessary, limited to the feasible parameter value-range.

It is also provided that the created protocol and the implementable sequence are transferred via the communication interface to the MARS computing unit for calculating the real-time instructions for controlling one (or a plurality of) MR-scanner system(s) in the fleet of MR-scanner systems.

Within the meaning of the present disclosure, a reconstruction algorithm refers to the procedure for creating images for medical assessment from the captured MR-scanner raw data. The MR-scanner raw data is acquired in what is called k-space. Said k-space corresponds to a representation of objects in the spatial frequency domain. A direct reconstruction using the fast Fourier transform (amongst others), is often performed to generate therefrom diagnostic information in the image domain. Reconstruction techniques can comprise, for example, parallel imaging, compressed sensing, or machine learning.

The present disclosure is based on the knowledge that there is a need for a method and a system for controlling a fleet of MR-scanner systems, which is characterized by an external device having a user interface. The method and system according to the disclosure may ensure that the user interface is universal or standardized for each MR-scanner system in the fleet, and control and/or operation may be performed. It is also ensured that the user interface and the implementation thereof has a consistent or identical design for each MR-scanner system in the fleet, allowing easier operation and more efficient control and implementation of a radiological examination.

The present disclosure advantageously decouples (in hardware and in software) the actual workflow (relating to the MR measurement) and the portion of the user interface, and also decouples the implementation thereof from the MR-scanner system. As one example, the user-interface portions are shifted to an external device. This outsourcing includes setting relevant parameters (protocol) for the individual sequences via the user interface or obtaining the relevant parameters from predetermined configuration parameters of the user interface. The resulting combination of a sequence and the protocol may be transferred to the MR-scanner system. It is verified by the transfer of the sequence to the MR-scanner system whether the relevant sequence is held in the MR-scanner system, and also whether the relevant sequence is the necessary and correct version.

It is also advantageous that it is possible to operate and run different MR-scanner systems simultaneously. In addition, a fleet of MR-scanner systems may be linked as a single MR-scanner system to an HIS (hospital information system) via the external device, and patients may be allocated to the fleet by dedicated software that takes account of the associated hardware specification of the MR-scanner system.

The present disclosure also achieves that updating the software of the MR-scanner systems, which is associated with long installation times and downtimes, no longer needs to be performed so frequently. Moreover, a technician is no longer needed on site to install or update the software. A new version of the software does not involve changes at the location of the MR-scanner system, but rather is implemented centrally via the external device and the corresponding workflow and imaging.

By virtue of the embodiment according to the disclosure, there is no need to keep extra computing power or an additional computer at the MR-scanner system, because the MR-scanner raw data is transferred via the relevant interfaces to the external device for performing the reconstruction. Moreover, there is no need for any complicated remote control of the MR-scanner system.

In an embodiment of the disclosure, the user interface is generated on the external device. Advantageously, the user interface is designed to edit the parameters, and is generated specifically accordingly. The user interface may be in the form of an analog interface having signal lamps, indicator panels, screen and input peripherals, etc. In a further embodiment, the user interface may be a digital interface comprising software and having a visualization system. For example, the external device may be provided as a computer (e.g. PC) having input peripherals, as a touchscreen having input and output functionality, as a terminal having a connection to a computer or to a Cloud-hosted computer running software for processing the inputs and outputs, etc. A user may control the MR-scanner system via the user interface.

In a further embodiment, the MARS computing unit does not have a user interface. Furthermore, the MARS computing unit is controlled via the user interface of the external device. The MARS computing unit may comprise a workstation and/or server hardware, as is generally known, that does not comprise or need a user interface for direct communication with a user/operator. The sequence and the parameters contained in the protocol are provided to the MARS computing unit via a communication interface. The MARS processing unit comprises at least one specific plug-in card, which works in real time independently of the operating system and provides the real-time instructions needed for the electronically-controllable components. The data necessary for generating the real-time instructions is transferred and provided by the combination of the sequence and the protocol. There is no need for additional access to the MARS computing unit.

In general, one or more plug-in cards may be formed on the MARS processing unit and/or on the other computer instances (host, Cloud, etc.). This/these plug-in card(s) can be formed externally, and connected to the computer via a suitable interface (e.g. proprietary/thunderbolt/USB/Ethernet/PCIe, OCuLnk, etc.).

In a further embodiment, the generated user interface formed on the external device has a standardized design for the MR-scanner systems in the fleet of MR-scanner systems. The generation of the UI may be performed on the external device or on a separate computer and transmitted to the external device, which provides greater flexibility. The same user interface, e.g. an embodiment in software, may advantageously be used for all the MR-scanner systems in a fleet. For example, the latest software version may be used for communicating with each MR-scanner system. In the user interface, it is only the integrating of the parameters to be entered and their processing in the sequence and of the protocol that is adapted for the particular MR-scanner system.

In a further embodiment, a plurality of MR-scanner systems are controlled via the one user interface formed on the external device. It can be provided e.g. that MR-scanner systems in different designs are controlled via the one user interface formed on the external device. The user interface may comprise a software version that may be used to operate each of the MR-scanner systems. The latest software version is installed, for example. For performing the MR measurement, only the parameters entered by the user/operator that is adapted specifically for each MR-scanner system may be processed.

In a further embodiment, it is provided that a plurality of MR-scanner systems, which e.g. are of different designs, are controlled in parallel. Thus, it is possible via the user interface to access in a standardized manner MR-scanner systems in different designs having a different field of use and a different hardware configuration, and to receive and convert into an appropriate protocol and sequence, parameters for an MR measurement.

In a further embodiment, the external device comprises a control unit. The control unit is designed to perform at least one reconstruction algorithm for reconstructing images from the captured MR-scanner raw data. In addition, an interface is provided for communicating with the MARS computing unit via the communication interface. A reconstruction algorithm may be performed by means of the control unit, for instance a processor unit. With regard to processing power, the external device may advantageously be designed such that the complex and computationally-intensive reconstruction of the MR-scanner raw data may be performed on the external device. Hence, there is no need to provide an additional processing unit for the reconstruction directly at the MR-scanner system.

In a further embodiment, the communication interface is designed to transfer status information to the external device. The external device is advantageously designed to receive and process inputs by a user/practitioner. The external device is also designed to provide and/or output to the user/practitioner the status information received from an MR-scanner system, on the basis of which information the user/practitioner may monitor a measurement process and the MR-scanner system and make suitable adjustments if necessary or desirable.

In a further embodiment, the communication interface implements, for communication, a Digital Equipment Corporation (DEC)net network protocol. DECnet is a homogeneous local area network for networking the MR-scanner system to the external device by means of a point-to-point network architecture.

In a further embodiment, the communication interface implements, for communication, an Internetwork Packet Exchange (IPX)/ Sequenced Packet Exchange (SPX) network protocol. IPX is a connectionless proprietary protocol that has routing capabilities. The IPX-based SPX (Sequenced Packet Exchange) protocol implements secure and connection-oriented communication.

In a further embodiment, the communication interface implements, for communication, a Transmission Control Protocol/Internet Protocol (TCP/IP) network protocol. The TCP/IP network protocol comprises a group of network protocols comprising the Internet Protocol (IP), the Transmission Control Protocol (TCP) and the User Datagram Protocol (UDP), and also the Internet Control Message Protocol (ICMP). IP addresses are used to identify the network nodes.

A secure communication connection between the external device and the MR-scanner system is provided by means of the network protocols mentioned.

In a further embodiment, the MARS computing unit and the hardware layer communicate via a local communication connection. The local communication connection comprises at least one serial communication connection and/or a local Ethernet connection. The real-time instructions may be transferred to field programmable gate arrays (FPGAs) and/or to the digital signal processors via the serial communication connection and the local Ethernet connection. The real-time instructions are converted into control commands for the electronically-controllable components.

In a further embodiment, changes to the parameters for creating the protocol are implemented centrally. In a further embodiment, the protocol and the implementable sequence are rolled out to all (or selected) MR-scanner systems in the fleet of MR-scanner systems in response to a trigger command. The parameters for the associated MR measurement can advantageously be provided by an operator/user at a central device (external device) and, on confirmation, rolled out to the selected (or all) of the MR-scanner systems registered in a fleet. The maintenance effort and downtime of the individual MR-scanner systems may thereby be reduced.

Achieving the object was described above with reference to a method. Features, advantages, or alternative embodiments mentioned in this connection may also be applied equally to the other claimed subject matter, and vice-versa. In other words, the embodiments that relate to a system or a computer program product, for example, may also be developed by combining features described or claimed in connection with the method embodiments. The corresponding functional features of the method are implemented in this case by corresponding physical modules, e.g. by hardware modules or microprocessor modules, of the system or product, and vice-versa.

According to a further aspect, the disclosure relates to a system for controlling a fleet of MR-scanner systems. The system is designed to perform the method according to the disclosure.

The system comprises an external device. The external device is configured to generate and/or design a user interface for editing parameters for creating a protocol for a sequence, which may be implemented on an MR-scanner system according to transmitted system attributes of an MR-scanner system. As already mentioned in connection with the method, the user interface may also be generated on another device and then transferred as control data for output of the UI buttons and fields.

The system according to the disclosure also comprises an MR-scanner system having system attributes, which are transmitted to the external device via a communication interface.

The created protocol is transferred via the communication interface to a MARS computing unit of the MR-scanner system for calculating the real-time instructions for controlling one (or a plurality of) MR-scanner system(s), in the fleet of MR-scanner systems.

According to a further aspect, the disclosure relates to a method for reconstructing images from MR-scanner raw data captured by at least one MR-scanner system from a fleet of MR-scanner systems. The MR-scanner systems are controlled by a method according to the first aspect of the present disclosure.

The method comprises a plurality of method steps. In a first method step, an MR-scanner system captures raw data, and a MARS computing unit provides the captured raw data.

In a further method step, an external device receives the raw data via a communication interface.

In a further method step, it is provided to perform at least one reconstruction algorithm. The reconstruction algorithm is performed on a control unit of the external device. Performing the reconstruction algorithm implements a reconstruction of images from the captured MR-scanner raw data.

The above-described embodiments according to the disclosure of the two methods (for controlling the fleet and for the reconstruction) may also be implemented, according to the disclosure, as a computer program, wherein a computer is caused to execute the above-described method according to the disclosure when the associated computer program is executed on an electronic device, component, and/or computer of the hardware layer or on a processor of the computer, e.g. the control unit of an external device. The associated computer program may be provided as a signal by download, or may be stored in a memory unit of the computer with computer-readable program code contained therein to cause the computer to execute instructions according to the aforementioned method. In addition, the associated computer program may also be stored in a machine-readable storage medium. An alternative way of achieving the object of the present disclosure is to provide a storage medium that is implemented for storing the above-described method and may be read by a computer or processor.

The above embodiments, configurations, and developments may be combined with one another in any practical way. Further possible embodiments, configurations, developments, and implementations of the disclosure also include combinations of features of the disclosure that are described above or below in relation to exemplary embodiments, even if these combinations are not mentioned explicitly. For instance, a person skilled in the art may add individual aspects as improvements or additions to the relevant basic form of the present disclosure

BRIEF DESCRIPTION OF THE DRAWINGS/FIGURES

Exemplary embodiments, which shall not be interpreted in a restrictive sense, and their features and further advantages are discussed in the following detailed description of the figures with reference to the drawing, in which.

The same reference signs are used to denote identical or functionally equivalent elements.

DETAILED DESCRIPTION

The disclosure relates to controlling a fleet of MR-scanners. In one exemplary embodiment, an MR-scanner may comprise the following components for a Syngo system:

- a magnetic resonance system (MR-scanner);
- a MARS processor for measurement and image reconstruction;
- a communication interface to an external device having a user interface and e.g. having a Syngo Acquisition Workplace for operating the Syngo MR system.

Figure 1:
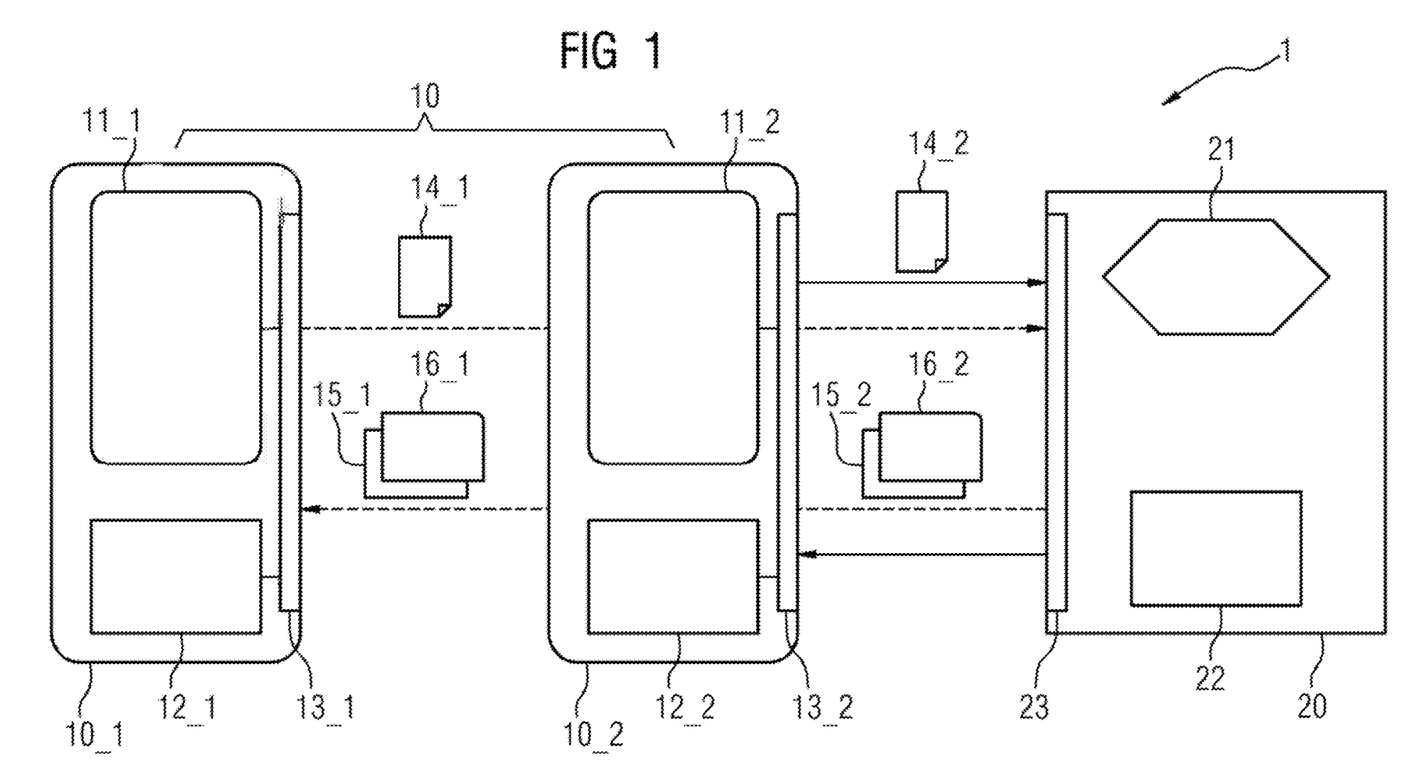
FIG. 1 is a schematic diagram for illustrating an example system according to an embodiment of the disclosure.

FIG. 1 is a schematic diagram for illustrating an example system according to an embodiment of the disclosure. In FIG. 1, reference number 10 denotes a fleet of MR-scanner systems 10_1, 10_2. FIG. 1 shows an example of an embodiment of the system 1 for controlling a fleet 10 of MR-scanner systems 10_1, 10_2 and for implementing a method according to the present disclosure. A fleet 10 may also comprise further MR-scanner systems not shown, and is not restricted to the embodiment shown, e.g. to the number of MR-scanner systems 10_1, 10_2.

The fleet 10 comprises an MR-scanner system 10_1, 10_2. Each MR-scanner system 10_1, 10_2 comprises a respective hardware layer 11_1, 11_2. The hardware layers 11_1, 11_2 each comprise a plurality of any suitable electronically-controllable components and mechanical components configured to perform an MR measurement and capture MR-scanner raw data. The electronically-controllable components comprise transmit and receive coils (TX, RX) and gradient magnetic coils, as well as the acquisition hardware peripherals for the patient to be examined. The electronically-controllable components are interfaced in software via hardware-component driver stages, and may be addressed via an FPGA and/or DSP. Suitable libraries may be used for the interfacing. The FPGA and/or DSP provide the interface for the real-time instructions and for converting the instructions into appropriate control signals for the electronically-controllable components. The mechanical components comprise each of the components needed to operate the MR-scanner system 10_1, 10_2 and to capture MR-scanner raw data. This also includes a patient table and the MR-scanner block, into which a patient is moved while lying on the patient table.

The MR-scanner systems 10_1, 10_2 further comprise, respectively, a MARS computing unit 12_1, 12_2. Each of the MARS computing units 12_1, 12_2 is designed to implement a respective measurement framework 18_1, 18_2 using a respective sequence 16_1, 16_2, to calculate respective real-time instructions 17_1, 17_2, and to transmit these instructions to the components of the respective hardware layer 11_1, 11_2 for controlling the respective MR-scanner systems 10_1, 10_2. The MARS computing unit 12_1, 12_2 may be in the form of a standardized workstation. The MARS computing unit may be provided at least one specific plug-in card, which works in real time independently of the operating system and provides the real-time instructions needed for the electronically-controllable components.

In addition, the MR-scanner systems 10_1, 10_2 each comprise a respective communication interface 13_1, 13_2 for communicating with an external device 20. In one embodiment, the communication interfaces 13_1, 13_2 may comprise different network protocols for communication between the MR-scanner system 10_1, 10_2 and the external device 20. For example, the communication interface may use the DECnet, IPX/SPX, TCP/IP network protocol, etc. for communication.

The external device 20 has an interface for establishing communication with the communication interfaces 13_1, 13_2. The external device may also have a user interface 21 and a control unit 22. The user interface 21 may be integrated in the external device 20 so that the user interface 21 and the external device 20 are embodied as a contiguous unit (e.g. terminal, PC, with touchscreen). In an alternative embodiment, the user interface 21 may be in the form of a multiplicity of peripheral devices for the input (keyboard, mouse, microphone, switches, pushbuttons, etc.) and for the output (screen, display, etc.) of information, and have a communication connection (Bluetooth, LAN, WiFi, etc.) to a control unit 21, which is implemented in a separate peripheral device (Workstation, PC). It can also be provided that the external device 20 is implemented as software hosted on a server or in the Cloud and is addressed via a peripheral device (hand-held device, laptop, terminal, screen with input means, etc.) that is in communication with each MR-scanner system 10_1, 10_2.

Each MR-scanner system 10_1, 10_2 has specific system attributes predetermined by the respective built-in hardware layers 11_1, 11_2. The system attributes are respectively transmitted to the external device 20 via the communication interface 13_1, 13_2. For example, the MR-scanner systems 10_1, 10_2 may transfer the respective system attributes to the external device 20 in an automated manner as soon as a communication connection is established. Alternatively, a user/operator may retrieve the system attributes of the MR-scanner systems 10_1, 10_2 connected to the external device.

The user interface 21 formed on the external device 20 may be used to edit parameters for creating a protocol 15_1, 15_2. The protocol may be a parameterization of an MR measurement, which in combination with an implementable sequence 16_1, 16_2, is translated by a measurement framework 18_1, 18_2 (cf. FIG. 3) into the appropriate real-time instructions. Thus, a protocol is formed for a sequence 16_1, 16_2, which may be implemented on a respective MR-scanner system 10_1, 10_2, according to the transmitted system attributes of the MR-scanner system 10_1, 10_2.

The sequence 16_1, 16_2 and the generated protocol 15_1, 15_2 are transferred to the MARS computing unit 12_1, 12_2 via each respective communication interface 13_1, 13_2. The MARS computing unit 12_1, 12_2 may use the transferred sequence 16_1, 16_2 and the generated protocol 15_1, 15_2 to calculate the real-time instructions 17_1, 17_2 for controlling one (or a plurality of) MR-scanner system(s) 10_1, 10_2 in the fleet 10. For instance, the user interface 21 of the external device 20 may control a plurality of MR-scanner systems 10_1, 10_2, e.g. in different designs. In a further embodiment, MR-scanner systems 10_1, 10_2 in different designs may be controlled in parallel with one another. This makes it possible for an operator/user to operate and control a plurality of MR-scanner systems 10_1, 10_2 in the fleet 10 efficiently from the external device 20.

Figure 2:
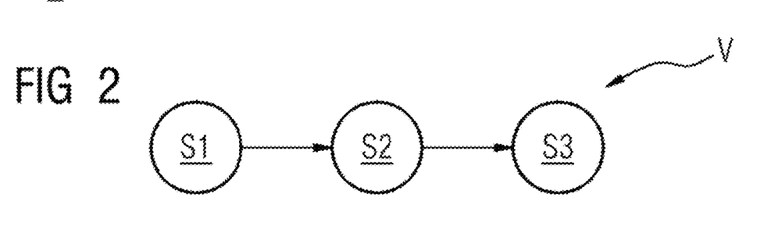
FIG. 2 is a flow diagram of an example method according to a further embodiment of the disclosure.

FIG. 2 shows a flow diagram of an example method V according to a further embodiment of the disclosure. The method V shown in FIG. 2 for reconstructing images from MR-scanner raw data captured by at least one MR-scanner system (e.g. 10_1, 10_2) from a fleet (e.g. 10) of MR-scanner systems (e.g. 10_1, 10_2) comprises a plurality of method steps S1-S3. In a first method step S1, an MR-scanner system (e.g. 10_1, 10_2) captures raw data, and a MARS computing unit (e.g. 12_1, 12_2) provides the captured raw data. In a second method step S2, an external device 20 receives the captured raw data via a communication interface (e.g. 13_1, 13_2). The external device 20 may again comprise a user interface 21 and a control unit 22. In a further method step S3, the control unit 22 of the external device 20 performs at least one reconstruction algorithm. The reconstruction algorithm is designed to reconstruct images for medical diagnosis from the captured MR-scanner raw data.

Figure 3:
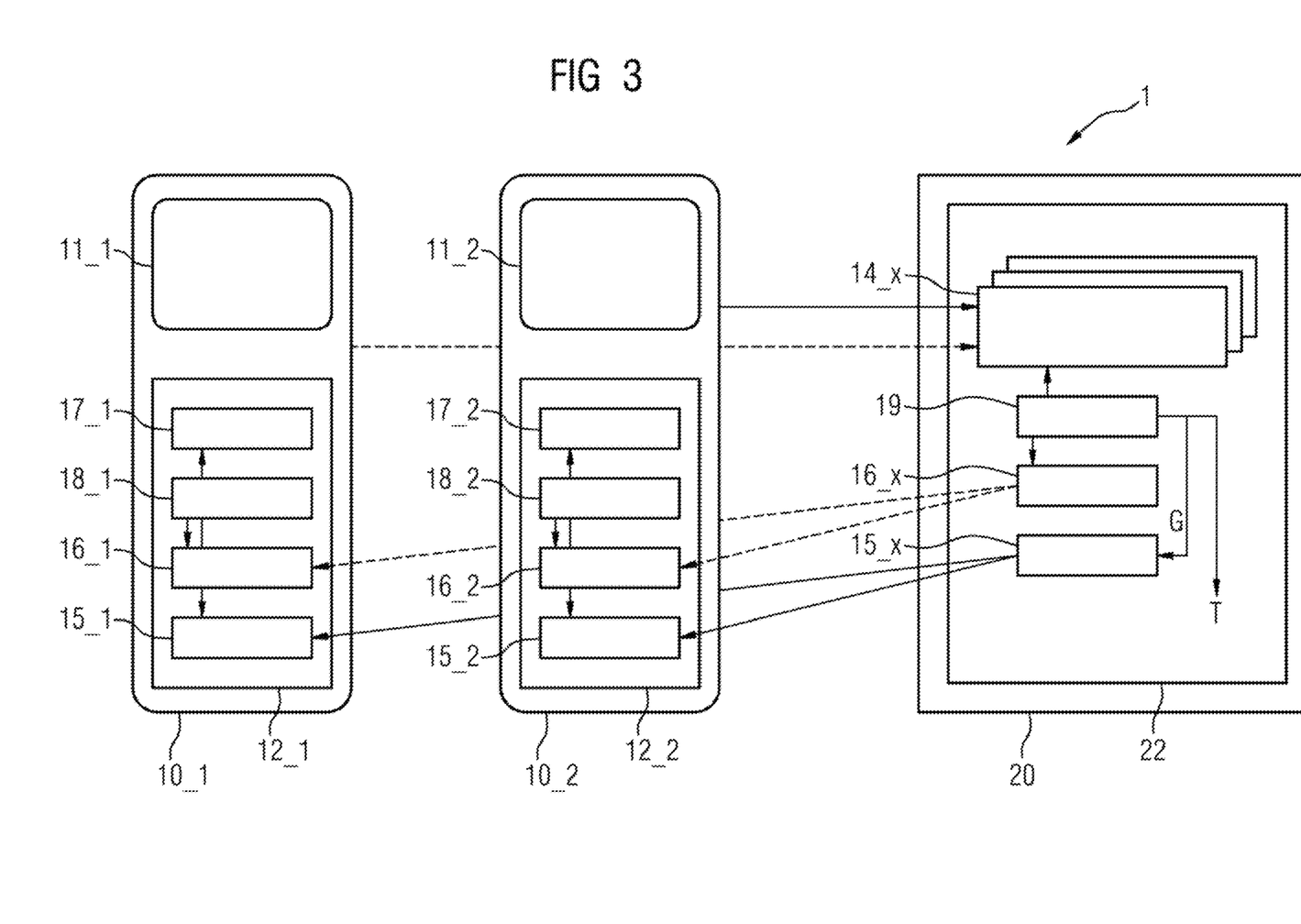
FIG. 3 is a schematic diagram for illustrating an example system according to a further embodiment of the disclosure.

FIG. 3 is a schematic diagram for illustrating the system 1 according to a further embodiment of the disclosure. In FIG. 3, reference sign 1 denotes the system for controlling a fleet 10 of MR-scanner systems 10_1, 10_2. The system 1 as shown in FIG. 3 comprises the same components as the system shown in FIG. 1. The system 1 shows two MR-scanner systems 10_1, 10_2 in the fleet 10 as a non-limiting example. The MR-scanner systems 10_1, 10_2 have a respective MARS computing unit 12_1, 12_2, a hardware layer 11_1, 11_2, and a communication interface 13_1, 13_2 (not shown). Each MARS computing unit 12_1, 12_2 may be in the form of a standardized workstation or computer. In an exemplary embodiment, different software versions may be executed on the processing unit (processor) of the MARS computing unit 12_1, 12_2. It is provided, for example, that software for controlling the MR-scanner system 10_1 is installed and executed with a version status v.2 on the MARS computing unit 12_1. It can also be provided, that software for controlling the MR-scanner system 10_2 is installed and executed with version status v.3 on the MARS computing unit 12_2. The respective MARS computing units 12_1, 12_2 perform, for the associated MR-scanner system 10_1, 10_2, the MR measurement for capturing the MR-scanner raw data and performing the reconstruction algorithm.

The system 1 as shown in FIG. 3 also comprises an external device 20 having a user interface 21 (not shown). The external device 20 comprises a processing unit 22 for executing software, for instance having version status v.11. The MR-scanner systems 10_1, 10_2 may be controlled and operated via the external device 20 even if software having a different version status is being executed thereon. The external device 20 uses the user interface 21 to form the connection to the MR-scanner systems 10_1, 10_2. A preferred or necessary MR measurement may be planned by means of the external device 20. For this purpose, the external device 20 may retrieve, or receive in an automated manner, system attributes 14_x specific to MR-scanner system 10_1, 10_2. By means of a software-implemented generic Exam-/Workflow-UI module 19 implemented on the processing unit 22, a protocol 15_x is generated using the specific system attributes 14_x and a sequence 16_x. The sequence 16_x is selected from a plurality of different sequences on the basis of user requirements. The sequences 16_x comprise instructions for different types of measurements that the user/operator may select. The sequences 16_x specify physical limits of the associated MR-scanner system 10_1, 10_2. Once the protocol 15_x has been generated, planning for an MR measurement is complete. The protocol 15_x may comprise parameters such as, for example, slices, position, resolution, echo time, repetition time, slice resolution, slice orientation, number of repetitions, averaging, image processing filters, etc. Thus the protocol 15_x comprises all the parameters relevant to an individual measurement.

The sequence 16_x used to generate the protocol 15_x, and the generated protocol 15_x, are transferred to each respective MR-scanner system 10_1, 10_2, e.g. to the MARS computer systems 12_1, 12_3, via a respective communication connection, e.g. via each respective communication interface 13_1, 13_2. Thus, the sequence and the generated protocol provide the interface between the external device 20 and the MR-scanner systems 10_1, 10_2.

The MR measurements of the MR-scanner system 10_1, 10_2 are performed by the associated MARS computing unit 12_1, 12_2. For this purpose, a measurement framework 18_1, 18_2 generates, on the basis of the generated and received protocol 15_1, 15_2 together with the associated sequence 16_1, 16_2, appropriate real-time instructions 17_1, 17_2 for controlling the hardware layer 11_1, 11_2, in particular for RF transmitters (TX), RF receivers (RX) and gradients. The generated real-time instructions 17_1, 17_2 are executed in a real-time controller (e.g. FPGAs, a DSP for highly precise timing, etc.) and output to the MR-scanner system 10_1, 10_2 in a coordinated manner By means of the real-time instructions 17_1, 17_2, each respective measurement framework 18_1, 18_2 provides RF pulses and gradients at the correct instant in time.

The sequence 16_1, 16_2 transmitted to each respective MARS computing unit 12_1, 12_2 and used to generate the real-time instructions 17_1, 17_2 has the same version status v.11 as is being run on the external device 20. For instance, for the Exam-/Workflow-UI module 19, the software versions undergo successive further developments. Likewise, the sequence is developed further to a lesser extent. The measurement framework 18_1, 18_2, on the other hand, is practically unchanged in terms of the fundamental attributes. By the use of stable interfaces between the sequence 16_1, 16_2 and the measurement framework 18_1, 18_2, for example by means of descriptive languages or by means of stable interfaces, for instance C-interfaces, the software versions executed on the MR-scanner systems 10_1, 10_2 may vary but can advantageously be addressed simultaneously by a common user interface 21 via the external device 20. For instance, different software versions may be run in combination and allow for simpler replacement. By virtue of this exemplary embodiment, a user/operator may work with the version of software installed on the external device 20, and control and operate a plurality of different MR-scanner systems 10_1, 10_2 in the fleet 10. As one example, a plurality of MR-scanner systems 10_1, 10_2 may be addressed and controlled simultaneously or in a time-interleaved manner via a remote connection.

According to the disclosure, all UI-related aspects for controlling the MR-scanner systems 10_1, 10_2 are outsourced. The user interface 21 (G), is generated on the external device 20. As one example, for all the MR-scanner systems 10_1, 10_2 in the fleet 10, UIs specific to each are generated on the external device 20, so that a plurality of users are also able to enter control instructions (parameters etc.) and work in parallel. The performance of the fleet 10 can thereby be increased overall.

The present disclosure intends that the MARS computing unit 10_1, 10_2 comprises just a minimum, or the maximum necessary, amount of software that is needed to perform an MR measurement. For example, it is intended that the amount of software provides only for HW support and handling individual MR measurement jobs (either at the instruction level or together with the sequences and protocols). The associated workflows, recon, QA, and image-storage components of the workflow-specific and application-specific software are decoupled and, for instance, implemented by an external device 20. It can be provided alternatively that these are implemented in a distributed manner on a plurality of Clouds.

By means of the external device 20 or, alternatively by means of web-enabled further devices, the users/operators/practitioners may access the Cloud(s) and plan the MR measurements to be performed. In addition, quality assurance (QA) of the initial clinical images (images reconstructed from the MR-scanner raw data) may be performed by means of the external device 20 having the user interface 20 or, according to a further embodiment, via a web-based user interface. The user/operator/practitioner need not be on site to perform the MR measurement, and, if applicable, a plurality of scanners may be operated simultaneously. The specific MR measurement jobs are transmitted, together with the sequence and the generated protocol, from the external device 20 to the MR-scanner systems 10_1, 10_2. According to a further embodiment, individual instructions (gradient, TX, RX) for each individual MR measurement may be transmitted directly from the external device to the MR-scanner systems 10_1, 10_2.

Developments to the software contents may be implemented solely in the external device 20. The software executed on the MR-scanner system 10_1, 10_2, e.g. on the MARS computing unit 12_1, 12_2, is stable and hence has stable interfaces. A software version may only be installed and suitably configured in the external device 20. The installation may take place in parallel with an MR-scanner system 10_1, 10_2 running a measurement, and put back into use without long downtimes.

In a further embodiment, it is provided to connect the external device 20 to a hospital planning system, and to allocate the patients across the fleet depending on the clinical issue, technical scanner requirements and operator expertise locally.

The various components described herein may be referred to as "units" or "modules." As described herein, these components may be implemented via any suitable combination of hardware and software components. This may include FPGAs, processors, processing circuitry, or other suitable hardware components configured to execute instructions or computer programs that are stored on a suitable computer readable medium. Thus, these components may alternatively be referred to herein as processors, or processing circuitry.

What is claimed is:

1. A method for controlling a fleet of magnetic resonance (MR)-scanner systems via a user interface, wherein each MR scanner system in the fleet of MR-scanner systems includes (i) a hardware layer having a plurality of electronically-controllable components and mechanical components to perform an MR measurement and acquisition of MR-scanner raw data, and (ii) a Measurement and Reconstruction System (MARS) computing unit, the method comprising:

transmitting, via a MR scanner system in the fleet of MR-scanner systems, respective system attributes to an external device, the system attributes identifying physical MR scanner limitations of the MR scanner system with respect to parameters used in accordance with a generated protocol for executing a sequence;

generating, via the external device, a user interface according to the transmitted system attributes to enable an adjustment of parameters for generating a protocol for a sequence that is implemented on the MR scanner system;

transferring the protocol and the sequence generated via the user interface to a respective MARS computing unit of the MR scanner system;

calculating, via the respective MARS computing unit of the MR scanner system, real-time instructions using the respectively generated protocol and sequence;

transmitting the real-time instructions to a hardware layer of the MR scanner system; and controlling the MR scanner system using the real-time instructions.

2. A system for controlling a fleet of MR-scanner systems via a user interface, comprising:

a MR scanner system in the fleet of MR-scanner systems configured to transmit respective system attributes via a communication interface, the system attributes identify physical MR scanner limitations of the MR scanner system with respect to parameters used in accordance with a generated protocol for executing a sequence;

an external device configured to generate a user interface for editing parameters for generating a protocol for a sequence, which is implemented on the MR-scanner system according to the transmitted system attributes, wherein the MR scanner system comprises a respective Measurement and Reconstruction System (MARS) computing unit configured to:
receive the protocol and the sequence generated via the user interface, and
calculate real-time instructions using the respectively generated protocol and sequence; and
control the MR scanner system using the real-time instructions.

3. The method as claimed in claim 1, further comprising:
controlling the respective MARS computing unit of the MR scanner system via the user interface of the external device, and
wherein the respective MARS computing unit of the MR scanner system has no user interface.

4. The method as claimed in claim 1, further comprising:
controlling a plurality of MR scanner systems in the fleet of MR-scanner systems via the user interface generated by the external device, and
wherein the plurality of MR scanner systems in the fleet of MR-scanner systems each has a different software version.

5. The method as claimed in claim 4, wherein the plurality of MR scanner systems are controlled in parallel.

6. The method as claimed in claim 1, further comprising:
executing, via the external device, a reconstruction algorithm to reconstruct images from MR-scanner raw data acquired via the MR scanner in the fleet of MR-scanner systems.

7. The method as claimed in claim 1, further comprising:
transferring, via a communication interface of the MR scanner system, status information to the external device.

8. The method as claimed in claim 1, wherein the act of transmitting the respective system attributes to the external device comprises:
transmitting the respective system attributes to the external device in accordance with a Digital Equipment Corporation ((DEC)net), Internetwork Packet Exchange (IPX)/Sequenced Packet Exchange (SPX), and/or Transmission Control Protocol/Internet Protocol (TCP/IP) network protocol, and
wherein the act of transferring the protocol and the sequence generated via the user interface to the respective MARS computing unit of the MR scanner system comprises:
transferring the protocol and the sequence generated via the user interface to the respective MARS computing unit of the MR scanner system in accordance with a DECnet, IPX/SPX, and/or TCP/IP network protocol.

9. The method as claimed in claim 1, wherein the act of transmitting the real-time instructions to the hardware layer of the MR scanner system comprises transmitting the real-time instructions to the hardware layer of the MR scanner system via a serial communication connection and/or a local Ethernet connection.

10. The method as claimed in claim 1, further comprising:
adjusting the parameters for generating the protocol for the sequence that is implemented on the MR scanner system centrally, and
wherein the act of transferring the protocol generated via the user interface to the respective MARS computing unit of the MR scanner system comprises:
transmitting the protocol and the sequence generated via the user interface to a plurality of MR scanner systems in the fleet of MR-scanner systems in response to a trigger command.

11. The method of claim 1, wherein the system attributes comprise a maximum gradient amplitude, a maximum pulse duty factor, and/or a maximum B1 amplitude capable of being generated by the MR scanner system in the fleet of MR-scanner systems.

12. The method of claim 1, wherein the sequence that is implemented on the MR scanner system in the fleet of MR-scanner systems is user-selectable via the user interface from among a plurality of sequences.

13. The method of claim 12, wherein:
the sequence is a user-selected sequence from among one of the user-selectable plurality of sequences,
the protocol is generated via the user interface using the user-selected sequence, and
the act of transferring the protocol and the sequence generated via the user interface to a respective MARS computing unit of the MR scanner system in the fleet of MR-scanner systems comprises transferring the protocol generated using the user-selected sequence and the user-selected sequence to the MR scanner system.

14. The method of claim 12, wherein each one of the plurality of sequences specifies physical limits of the MR scanner system in the fleet of MR-scanner systems based upon the system attributes.

15. The method of claim 1, wherein the sequence is a user-selected sequence from among one of the user-selectable plurality of sequences, and
wherein the protocol is generated for the MR scanner system in the fleet of MR-scanner systems via the user interface using a user-selected sequence.

* * * * *